US011682474B2

(12) United States Patent
Weldemariam et al.

(10) Patent No.: US 11,682,474 B2
(45) Date of Patent: Jun. 20, 2023

(54) ENHANCED USER SCREENING FOR SENSITIVE SERVICES

(71) Applicant: International Business Machines Corporation, Armonk, NY (US)

(72) Inventors: Komminist Weldemariam, Ottawa (CA); Srihari Sridharan, Nairobi (KE); Geoffrey Henry Siwo, Sandton (KE); Nelson Kibichii Bore, Lessos (KE); Solomon Assefa, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 158 days.

(21) Appl. No.: 16/218,434

(22) Filed: Dec. 12, 2018

(65) Prior Publication Data
US 2020/0194103 A1    Jun. 18, 2020

(51) Int. Cl.
*G16H 10/20* (2018.01)
*G16H 10/60* (2018.01)
(Continued)

(52) U.S. Cl.
CPC ............ *G16H 10/20* (2018.01); *G06N 20/00* (2019.01); *G16H 10/60* (2018.01); *G06N 3/08* (2013.01); *H04W 4/14* (2013.01)

(58) Field of Classification Search
CPC ........ G16H 10/20; G16H 10/60; G06N 20/00; G06N 3/08; H04W 4/14; G06Q 50/20–26
(Continued)

(56) References Cited

U.S. PATENT DOCUMENTS 5,572,421 A     11/1996  Altman et al.
7,593,952 B2 *   9/2009  Soll .................... G16H 20/40
(Continued)

FOREIGN PATENT DOCUMENTS

WO    WO2016010997 A1    1/2016
WO    WO2018022722 A1    2/2018
WO    WO-2019040279 A1 *  2/2019  ........... A61B 5/6802

OTHER PUBLICATIONS

Ricky Ho. (2012). Characteristics of Machine Learning Model. Blogger, all pages, horicky.blogspot.com/2012/02/characteristics-of-machine-learning.html.*
(Continued)

*Primary Examiner* — Jason S Tiedeman
*Assistant Examiner* — Jessica Marie Webb
(74) *Attorney, Agent, or Firm* — Barak Cohen; Otterstedt & Kammer PLLC (57) ABSTRACT

A first set of user data is received and a user profile is constructed based on the user data and in accordance with a sensitive service involving the user. A situational context is analyzed based on the first set of data. Personalized questions are generated, responsive to the user profile and to the situational context. The personalized questions are presented to a user corresponding to the user data and responses to same are received, including detection of user micro-expressions. The responses are analyzed, according to one or more machine learning models. A neural network model selects an action to be performed in response to analyzing the responses from the user; the action is a sensitive service involving the user. An apparatus is triggered to send a simple message service (SMS) message to a point of care service professional; the message recommends performance of the sensitive service on the user.

21 Claims, 6 Drawing Sheets

(51) Int. Cl.
  *G06N 20/00* (2019.01)
  *G06N 3/08* (2023.01)
  *H04W 4/14* (2009.01)

(58) Field of Classification Search
  USPC .......................................................... 705/2
  See application file for complete search history.

(56) References Cited

U.S. PATENT DOCUMENTS

| | | | | |
|---|---|---|---|---|
| 7,856,264 | B2* | 12/2010 | Firlik | A61M 5/14276 |
| | | | | 607/3 |
| 8,165,671 | B2* | 4/2012 | Freeman | A61H 31/005 |
| | | | | 607/5 |
| 8,602,789 | B2* | 12/2013 | Hallowell | A61B 3/113 |
| | | | | 434/167 |
| 8,719,298 | B2* | 5/2014 | Konig | G06F 16/951 |
| | | | | 707/706 |
| 9,201,573 | B1* | 12/2015 | Miles | G06F 9/451 |
| 9,729,403 | B1* | 8/2017 | Rabe | G06F 3/04895 |
| 10,262,384 | B1* | 4/2019 | Albro | G16H 20/00 |
| 10,390,718 | B2* | 8/2019 | Chen | A61B 5/721 |
| 10,446,273 | B1* | 10/2019 | McNair | G16H 10/60 |
| 10,705,796 | B1* | 7/2020 | Doyle | G06F 7/08 |
| 10,853,394 | B2* | 12/2020 | Kondadadi | G06F 40/35 |
| 2002/0035486 | A1 | 3/2002 | Huyn et al. | |
| 2003/0004788 | A1 | 1/2003 | Edmundson et al. | |
| 2003/0107596 | A1* | 6/2003 | Jameson | G06F 9/451 |
| | | | | 715/762 |
| 2004/0019502 | A1* | 1/2004 | Leaman | G16H 10/60 |
| | | | | 705/2 |
| 2005/0187929 | A1 | 8/2005 | Staggs | |
| 2006/0286520 | A1* | 12/2006 | Rosenberg | G09B 7/02 |
| | | | | 434/236 |
| 2007/0021981 | A1* | 1/2007 | Cox | G16H 40/20 |
| | | | | 705/2 |
| 2007/0053513 | A1* | 3/2007 | Hoffberg | G06K 9/00369 |
| | | | | 380/201 |
| 2008/0134077 | A1* | 6/2008 | Cheng | G06F 16/9577 |
| | | | | 715/781 |
| 2010/0092929 | A1* | 4/2010 | Hallowell | A61B 3/113 |
| | | | | 434/167 |
| 2012/0173319 | A1* | 7/2012 | Ferrara | G16H 20/10 |
| | | | | 705/14.4 |
| 2013/0073306 | A1* | 3/2013 | Shlain | G06Q 10/06 |
| | | | | 705/2 |
| 2013/0084554 | A1 | 4/2013 | Shah et al. | |
| 2013/0267795 | A1* | 10/2013 | Cosentino | A61B 5/746 |
| | | | | 600/301 |
| 2014/0108031 | A1* | 4/2014 | Ferrara | G16H 20/10 |
| | | | | 705/2 |
| 2014/0263423 | A1* | 9/2014 | Akdogan | G07F 11/00 |
| | | | | 222/23 |
| 2015/0287062 | A1 | 10/2015 | Shaffer et al. | |
| 2015/0370993 | A1* | 12/2015 | Moturu | G16H 50/50 |
| | | | | 703/6 |
| 2016/0063381 | A1 | 3/2016 | Allen et al. | |
| 2016/0196389 | A1* | 7/2016 | Moturu | G16H 10/60 |
| | | | | 705/2 |
| 2016/0361041 | A1* | 12/2016 | Barsimantov | G16H 50/30 |
| 2017/0055878 | A1* | 3/2017 | Chon | A61B 5/0077 |
| 2017/0069216 | A1* | 3/2017 | Vaughan | G16H 50/30 |
| 2017/0262609 | A1* | 9/2017 | Perlroth | G16H 10/60 |
| 2017/0323065 | A1* | 11/2017 | Proctor Beauchamp | |
| | | | | A61B 5/165 |
| 2017/0364637 | A1* | 12/2017 | Kshepakaran | G16H 10/60 |
| 2017/0365101 | A1* | 12/2017 | Samec | G02B 27/017 |
| 2018/0035932 | A1* | 2/2018 | Massova | A61B 5/14551 |
| 2018/0122509 | A1* | 5/2018 | Christiansson | G16H 40/63 |
| 2018/0197624 | A1* | 7/2018 | Robaina | G06F 3/012 |
| 2018/0278554 | A1* | 9/2018 | Kassabgi | G06F 40/56 |
| 2018/0301222 | A1* | 10/2018 | Dew, Sr. | G16H 15/00 |
| 2019/0042692 | A1* | 2/2019 | Betts-Lacroix | G16H 50/20 |
| 2019/0043610 | A1* | 2/2019 | Vaughan | G16H 50/20 |
| 2019/0043618 | A1* | 2/2019 | Vaughan | G16H 20/10 |
| 2019/0113973 | A1* | 4/2019 | Coleman | G06F 3/015 |
| 2019/0115104 | A1* | 4/2019 | Uske | G06F 11/3438 |
| 2019/0117151 | A1* | 4/2019 | Stern | G06T 7/0012 |
| 2019/0126014 | A1* | 5/2019 | Kapur | A61B 5/027 |
| 2019/0159675 | A1* | 5/2019 | Sengupta | A61B 5/7405 |
| 2019/0370834 | A1* | 12/2019 | Oppenheim | G16H 50/80 |
| 2020/0019642 | A1* | 1/2020 | Dua | G06N 3/0454 |
| 2020/0019863 | A1* | 1/2020 | Dua | G06F 40/216 |
| 2020/0098476 | A1* | 3/2020 | Loscutoff | G16H 50/70 |
| 2020/0160510 | A1* | 5/2020 | Lindemer | G06T 7/0012 |

OTHER PUBLICATIONS

Rabelo et al., "Development of a real-time learning scheduler using reinforcement learning concepts," Proceedings of 1994 9th IEEE International Symposium on Intelligent Control, Columbus, OH, USA, 1994, pp. 291-296.*

"Machine learning." Machine Learning—WaybackMachine, Dec. 7, 2017, 16:39, https://web.archive.org/web/20171213072744/https://en.wikipedia.org/wiki/Machine_learning.*

(N.a.), "Start Your Donation Today", Jun. 19, 2017, Inova Blood Donation, all pages, http://web.archive.org/web/20170619160555/https://www.inovabloodsaves.org/ (Year: 2017).*

Kim, K.H. et al., "Clinical applications of therapeutic phlebotomy", 2016, J Blood Med., 7: 139-144, all pages, https://www.ncbi.nlm.nih.gov/pmc/articles/PMC4957680/ (Year: 2016).*

(N.a.), "Should I open hints?", Nov. 9, 2017, Pearson Education, Inc., all pages, http://web.archive.org/web/20171109224940/https://help.pearsoncmg.com/mastering/student/standalone/TopicsStudent/take_hints_student.htm (Year: 2017).*

Oh Y-H, See J, Le Ngo AC, Phan RC-W and Baskaran VM. Jul. 10, 2018. A Survey of Automatic Facial Micro-Expression Analysis: Databases, Methods, and Challenges. Front. Psychol. 9:1128. doi: 10.3389/fpsyg.2018.01128. (Year: 2018).*

Peter Mell et al., "The NIST Definition of Cloud Computing". Special Publication 800-145. NIST. Sep. 2011, pp. 1-7.

Wikipedia, "Blood donation", https://en.wikipedia.org/wiki/Blood_donation, accessed Dec. 6, 2018. pp. 1-19.

Wikipedia, "Unified Medical Language System", https://en.wikipedia.org/wiki/Unified_Medical_Language_System, accessed Dec. 8, 2018, pp. 1-5.

John E. Kelly III, "Computing, cognition, and the future of knowing", IBM Corp. Oct. 2015. pp. 1-14. http://publicservicesalliance.org/wp-content/uploads/2015/10/Computing_Cognition_WhitePaper.pdf.

Oh YH, See J, Le Ngo AC, Phan RC, Baskaran VM. A survey of automatic facial micro-expression analysis: databases, methods, and challenges. Frontiers in psychology. Jul. 10, 2018;9:1128.

* cited by examiner

ENHANCED USER SCREENING FOR SENSITIVE SERVICES

BACKGROUND

The present invention relates to the electrical, electronic, computer and medical arts, and more specifically, to computerized screening tools.

Blood transfusion is a life-saving medical procedure, yet the demand across certain developing regions largely outstrips the supply, and the procedure can potentially be misused in some instances. According to the World Health Organization, certain developing regions meet only 50% of their required blood supply with only a subset of the countries in the developing regions meeting 80 to 100% of the required blood supply. While blood safety has improved tremendously over the last decade, providing safe blood is highly costly and is vulnerable to safety blind-spots. The blood supply chain from donor to recipient includes many complex processes and participants, which increases costs due to inefficiencies, threatens blood safety and creates artificial shortages due to unnecessary blood transfusions and loss of donated blood.

Currently, each time a donor walks into a donation center or site, he/she is required to complete a precompiled donor questionnaire, which includes questions related to life-style and health related questions. Once the questions are completed and consent is collected, a professional at the donation center assesses the donor responses and determines the next steps.

SUMMARY

Principles of the invention provide techniques for enhanced user screening for sensitive services. In one aspect, an exemplary method includes receiving a first set of user data; constructing a user profile that incorporates the first set of user data in accordance with a sensitive service involving the user; analyzing a situational context based on the first set of user data; generating personalized questions responsive to the user profile and to the situational context, according to the sensitive service involving the user, and presenting the personalized questions to a user corresponding to the user data; receiving and analyzing responses to the personalized questions from the user, including detection of user micro-expressions related to at least some of the responses; and triggering an apparatus to send a simple message service (SMS) message to a point of care service professional (e.g., care giver), the message recommending performance of the sensitive service on the user.

In another aspect, a non-transitory computer readable storage medium embodies computer executable instructions which when executed by a computer cause the computer to facilitate the method of receiving a first set of user data; constructing a user profile model that incorporates the first set of user data in accordance with a sensitive service involving the user; analyzing a situational context based on the first set of user data; generating personalized questions responsive to the user profile model and to the situational context, according to the sensitive service involving the user; presenting the personalized questions to a user corresponding to the user data; receiving responses to the personalized questions from the user; analyzing the responses from the user, using one or more machine learning models; selecting, by a neural network model, an action to perform in response to analyzing the responses from the user, wherein the action is a sensitive service to be performed on the user; and triggering the computer to send a simple messaging service (SMS) message that instructs a point of care service professional (e.g., care giver) to perform the selected action.

In yet another aspect, an apparatus includes a memory embodying computer executable instructions; and at least one processor, coupled to the memory, and operative, by executing the computer executable instructions, to facilitate a method of receiving a first set of user data; constructing a user profile model that incorporates the first set of user data in accordance with a sensitive service involving the user; analyzing a situational context based on the first set of user data; generating personalized questions responsive to the user profile model and to the situational context, according to the sensitive service involving the user; presenting the personalized questions to a user corresponding to the user data; receiving responses to the personalized questions from the user; analyzing the responses from the user, using one or more machine learning models; selecting, by a neural network model, an action to perform in response to analyzing the responses from the user, wherein the action is a sensitive service to be performed on the user; and triggering the processor to send a simple messaging service (SMS) message that instructs a point of care service professional (e.g., care giver) to perform the selected action.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

In view of the foregoing, techniques of the present invention can provide substantial beneficial technical effects. For example, one or more embodiments provide one or more of:

Efficient generation of highly personalized questionnaires for enhanced screening of users for sensitive services.

Analyzing, structuring and storing of plurality of user data according to health category, lifestyle category, and domain category to be used in screening of users for sensitive services.

Determining the occurrence of user events from a plurality of data sources in relation to screening for sensitive services.

Predicting the occurrence of a user's events to affect the user's eligibility to participate in the sensitive service.

Intelligently analyzing a user's responses corresponding to each question by determining a plurality of machine learning models, including analyzing histories of user responses for the same or similar question(s), user social media activities, cognitive state, scope of questionnaire responses of other respondents of a similar demographic, medical, social profile, and so on.

Generating contextual clues for questions such as providing textual, audio/video or graphical hints to explain a questions based on the user cohort analysis.

Predicting or selecting actions (e.g., blood test prioritization) in response to the analysis of the user responses.

These and other features and advantages of the present invention will become apparent from the following detailed description of illustrative embodiments thereof, which is to be read in connection with the accompanying drawings.

DETAILED DESCRIPTION

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
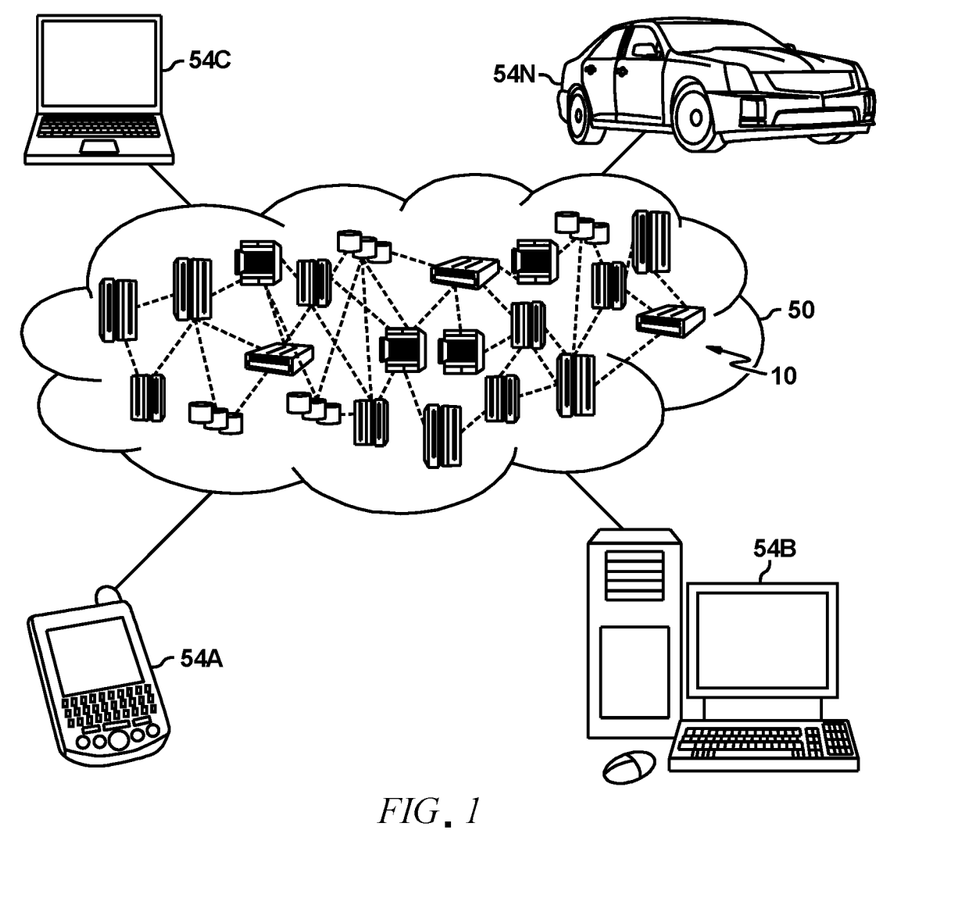
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
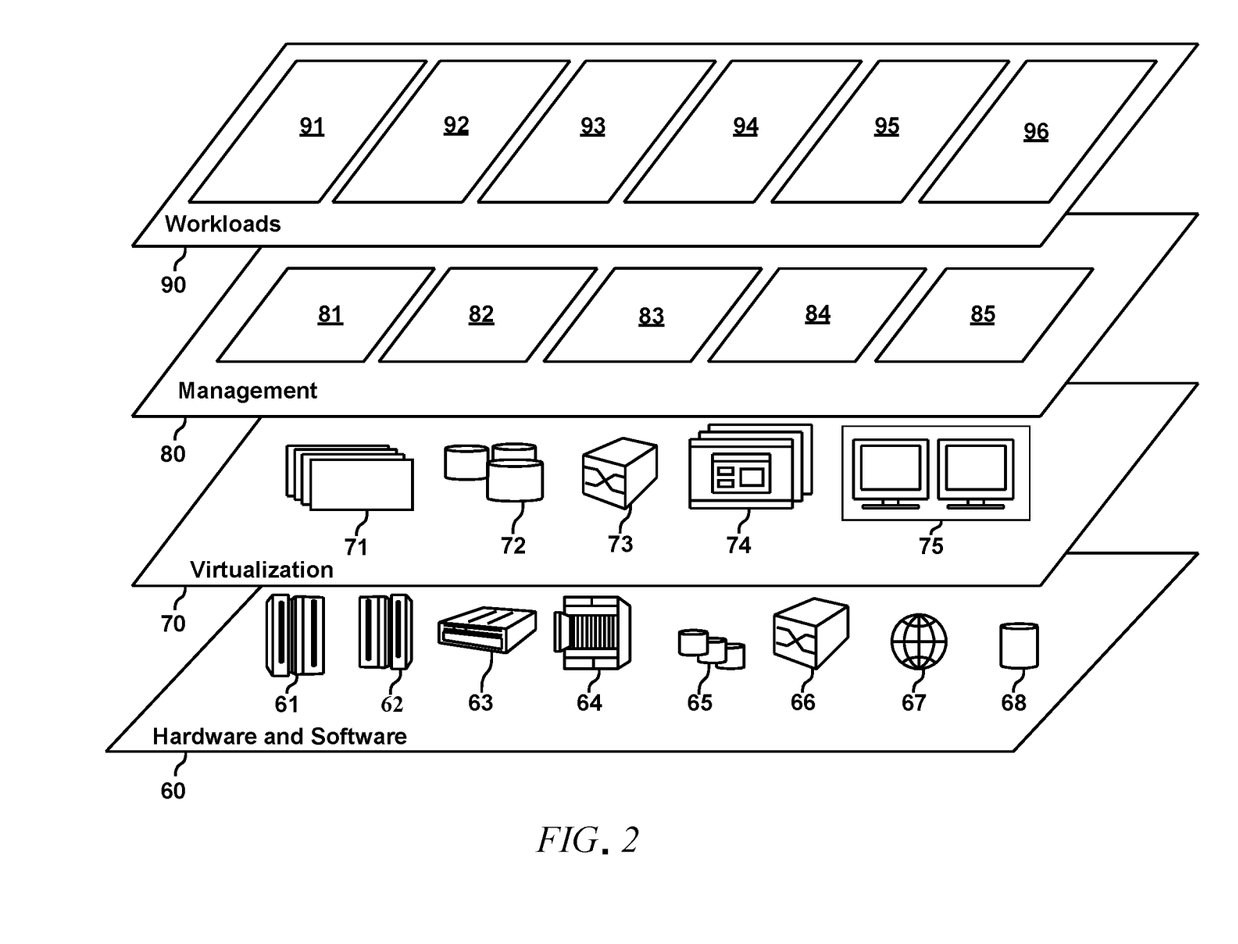
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and user screening system 96.

In typical user screening for blood donation, qualification questionnaires may be regulated by medical regulatory agencies. This may restrict the use of personalization as there is a risk that donor questionnaires are uniform to all donors irrespective of factors particularly pertinent to sensitive services such as blood donation, e.g., age, gender, location, etc. although one donor's activities (e.g., travel history, dietary condition) may completely differ from others. Some information that may affect the outcomes of blood donation can easily be missed from being collected. For example, the donor demographic, social, or travel history may expose the donor to diseases or conditions which are not routinely screened for in blood donation but could potentially influence compatibility with the recipient. Alternatively, without focused screening questions, there may be false indications of conditions that would prevent blood donation but which are not actually present.

Additionally, there currently is no way to up-front verify information provided by a donor (a donor may not recall past activities; forget to provide more details such as location/ places visited, past dietary condition, etc.).

Figure 3:
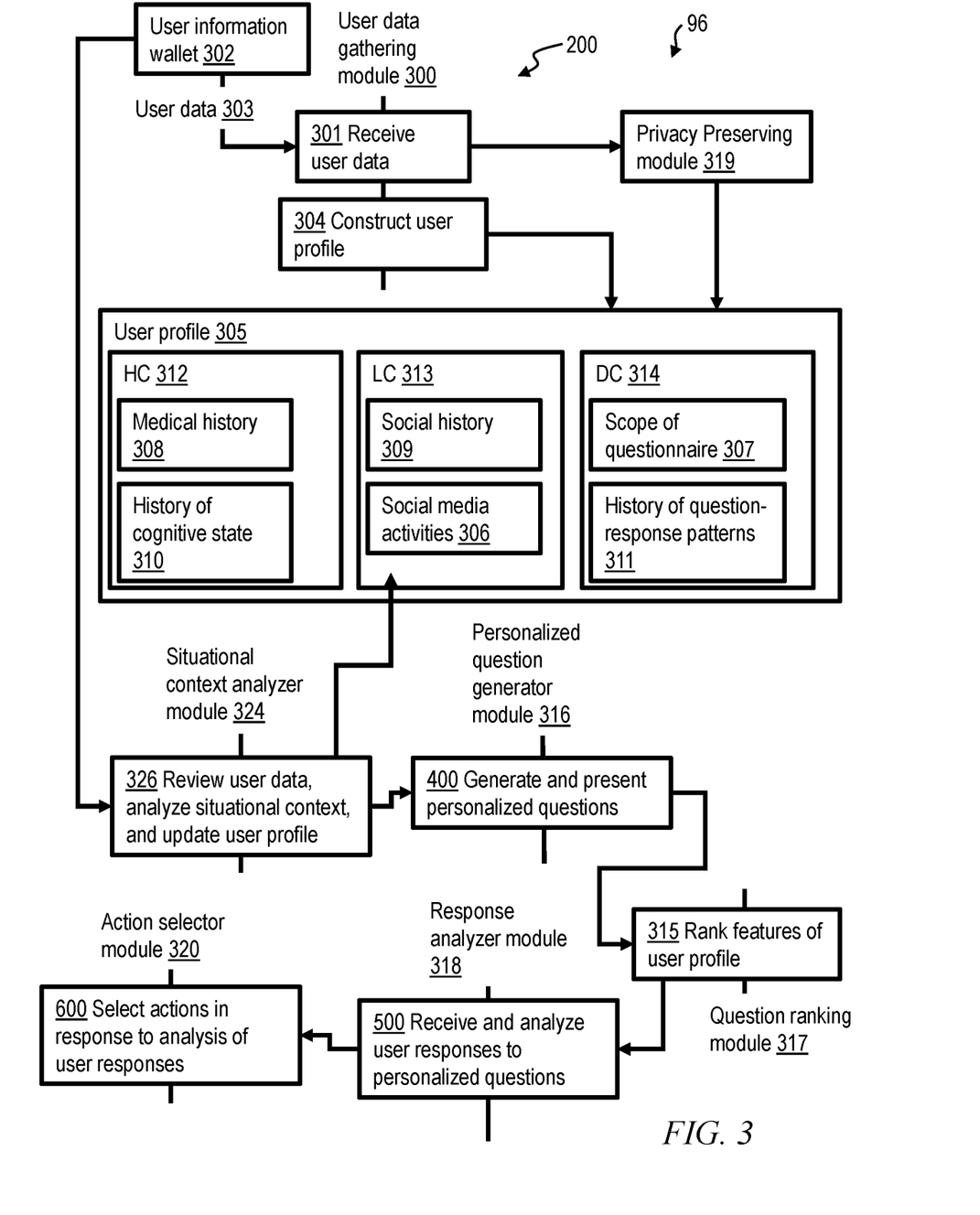
FIG. 3 depicts main components and steps of a system and method for enhanced user screening for sensitive services.

Certain aspects of the invention provide solutions to at least some of these exemplary problems, and to other problems. For example, as shown in FIG. 3, the user screening system 96 implements a method 200 that includes at 301 a user data gathering module 300 receiving from a user information wallet 302 a first set of data 303 that describes a user, and at 304 constructing a user profile 305 (based on the first set of user data). As part of step 304, the system 96 identifies the user using any of: biometrics (e.g., fingerprint, face detection, voice-based, biometric-enabled card), passcode, mobile application, etc. Appropriate privacy protections should be implemented—for example, in one or more embodiments, the user's informed consent is obtained prior to initiating the method 200.

The system 96 includes a personalized question generator module 316 that implements a method 400 (further described with reference to FIG. 4) for generating and presenting a set of personalized questions for screening the user for a sensitive service (e.g., blood donation). The system 96 also includes a response analyzer module 318 that implements a method 500 (further described with reference to FIG. 5) for assessing a set of user responses to personalized questions. Furthermore, the system 96 includes an action selector module 320 that implements a method 600 (further described with reference to FIG. 6) for selecting actions (e.g., blood collection, lab testing prioritization, etc.) in response to the analysis of the user responses.

Still referring to FIG. 3, the user profile 305 includes social media activities 306, scope of questionnaire 307 which defines the purpose of questionnaire (e.g., screening for generic or specific blood donation, organ donation, stem cell donation, or for other sensitive services), medical history 308 and social history 309, history of cognitive state 310, history of question-response patterns 311, etc. The user profile 305 may also contain references to one or more users who share similar demographic context, without revealing the users' privacy. The method of generating the user profile further characterizes the analyzed data into three categories: health category 312, lifestyle category 313 (e.g., travel history, dietary condition, etc.), and domain category 314 by determining the occurrence of a user event in the first set of user data 303. Examples of user events stored in the first set of user data or database include data related to the user visits to one or more locations or places within time thresholds (e.g., for the last 3 months), dietary conditions over a period of the past weeks, etc. Each of the occurrences of these user events are analyzed to determine their corresponding categories.

The HC (Health Category) 312: $<f_{h,1}, f_{h,2}, \ldots, f_{h,N}>$ includes features related to health of the user extracted from the user/donor history, medical/medication history from user computing devices (e.g., mobile phone, wireless wearable activity tracker), etc. The LC (Lifestyle Category) 313: $<f_{1,1}, f_{1,2}, \ldots, f_{1,K}>$ includes features related to the user lifestyle such as social group, dietary conditions/style, etc. The DC (Domain Category) 314: $<f_{g,1}, f_{g,2}, \ldots, f_{g,M}>$ includes features related to situational context (e.g., predicted disease outbreak, weather information, etc.). The DC is used to identify a user who should be further explored medically regarding qualification for a sensitive service.

In one or more embodiments, the question generation features are features generally in the machine learning sense, and are used by the personalized question generation module 316 and by a question ranking module 317, which at 315 ranks each feature i ($f_{i,j}$) j in each category j of the user profile 305 based on a risk analysis. The generated questions also are ranked according to a user cohort analysis, specific characteristics of a service for which a user is under screening, weights associated with each of the questions, and format of the questions to be presented for the user. In one scenario, the risk analysis further includes analyzing whether the user social or travel history is likely to have exposed the user to diseases or conditions that are predicted to affect the user's eligibility to participate in the sensitive service, e.g., by potentially influencing blood donation compatibility with a recipient. The risk analysis is part of a situational context analyzer module 324. In another embodiment, the feature sets (across the three categories) are used to identify question generation features that will be used by the personalized question generator module 316.

A privacy preserving module 319 adds extra privacy protection layers for user data within a data structure that contains identifiers of the user profile but anonymizes, obfuscates and/or generalizes the data so specific details about the user are not revealed. In one embodiment, a method of specifying one or more privacy-preserving rules includes specifying the aspect of obfuscating or hiding the privacy of the user but lets the system consume the user data and information for the purpose of screening a user or cohort of users for one or more sensitive services.

In one or more embodiments, the system 96 also includes a situational context analyzer module 324 that at 326 reviews the user data 303 and informs the personalized question generator module 316 regarding context that could affect what questions should be asked. For example, the situation context analyzer module 324 detects an emerging disease M outbreak in location X where a user has travelled within a predetermined time period before the time that a questionnaire is to be delivered to the user. The situational context analyzer module 324 infers the outbreak of disease M, and the user's travel history, from various aspects of the user data 303, e.g., social media activities 306. Symptoms of the disease M include A, B, C and medical history 308 indicates the user has taken a medicine P for symptom C; while for disease N (which is contra-indicated for user participation in the sensitive service for which the user will be screened), the common symptoms include C, D, E and treatments include medicine Q. The situational context analyzer module 324 updates the user HC 312 with the location X and medication history, and updates the user DC 314 with situational analysis results along with timestamp, including disease models, symptom analysis, drug interactions, and so on. In one or more embodiments, the DC 314 may be formatted at least partially in Unified Medical Language System in order to enhance data interchange and level of detail.

Figure 4:
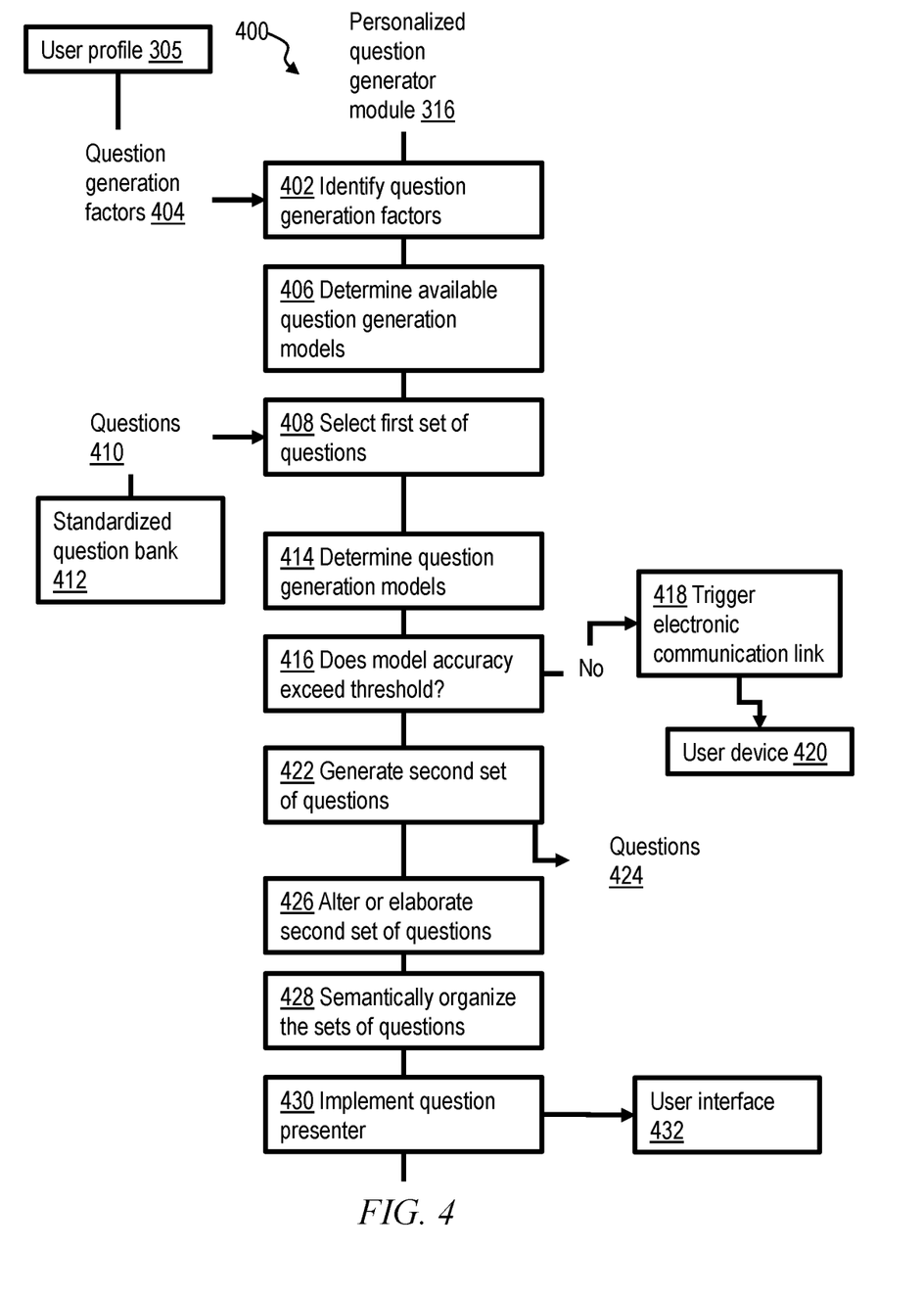
FIG. 4 depicts a flowchart of a method implemented by an exemplary question generator module of the system shown in FIG. 3.

FIG. 4 depicts steps of the method 400 that is implemented by the personalized question generator module 316. At 402, the personalized question generator module 316 identifies question generation features 404 in the user profile 305. At 406, the personalized question generator module 316 then determines a plurality of available question generation models based on the determined occurrence of a user event on the user data 303, the user profile 305, and the question generation features 404. At 408, the personalized question generator module 316 selects a first set of questions 410 from a standardized question bank 412, based on one or more rules (rules based on information from the user profile).

At 414, the personalized question generator module 316 determines question generation models based on the determined occurrence of the user event, the first set of user data 303, and the question generation features 404. At decision block 416, if the accuracy of the question generation models does not exceed a threshold, then at 418 the personalized question generator module 316 triggers an electronic communication link to a user device 420 of a human expert who further reviews a plurality of available question generation models and generated questions, then selects an optimal question generation model. Thus, the human expert trains the personalized question generator module 316 by specifying additional context for the questions. The initial threshold values are set by experts and over time, the system 96 learns better performing threshold values based on historical data, including historic threshold data.

At 422, the personalized question generator module 316 generates a second set of contextualized questions 424 using features from the three categories (lifestyle category 313, health category 312, and domain category 314). Using the above example about diseases M and N, the personalized question generator module may assess the user's history of symptoms and medications related to M and N; for example, the second set of questions may include questions about whether the user has been prescribed additional medications related to the disease N. The generated secondary set of questions are dynamically adjusted based on the user cohort. In one or more embodiments, one or more of the second set of questions can be answered with reference to the user profile 305 without requiring direct user intervention.

At 426, the personalized question generator module 316 further alters or elaborates the second set of questions based on the result of a user cohort analysis (e.g., education level, age, demographic, etc.) while preserving the essence of the questionnaires that need to be collected. Elaborating a question further includes providing textual, audio/video or graphical hints to explain the question based on the user cohort analysis.

In one or more embodiments, the personalized question generator module 316 uses varied and sophisticated computer reasoning methods (e.g., Bayesian methods, knowledge graph based techniques, deep learning algorithms such as Recurrent Neural Networks) to recommend contextualized questions for the user based on features from the three categories HC, LC, DC. In one or more embodiments, the personalized question generator module may take into consideration service site characteristics, which may vary as sensitive services can be offered by mobile units (i.e., mobile service site) in different parts of a country. For example, in embodiments specifically related to blood donation, varying donation site characteristics can include, e.g., geographic location that is extracted, e.g., from a user device geographic positioning system, weather at the specific day of donation that is extracted, e.g., by a user device from a weather station based on the geographic location, time of donation that is extracted, e.g., from a clock of a user device, altitude (may affect blood levels) that is extracted, e.g., from a pressure sensor of a user device, news stories of the area that are extracted, e.g., by a user device from a news service, etc. In one or more embodiments, the question generator module may take into account responses by other users who are similar to a given user in demography, medical history, social profile, etc.

In one or more embodiments, at 428 the personalized question generator module 316 semantically organizes the first and second set of questions. In one or more embodiments, at 428 the personalized question generator module 316 employs a multi-grained deep semantic similarity algorithm to evaluate questions' semantic similarity by deep semantic learning and domain cognitive modeling. At 430, the personalized question generator module 316 implements a question presenter that displays the questions via one or more user interfaces 432 such as on an adaptive GUI or by an interactive voice recognition interface.

Figure 5:
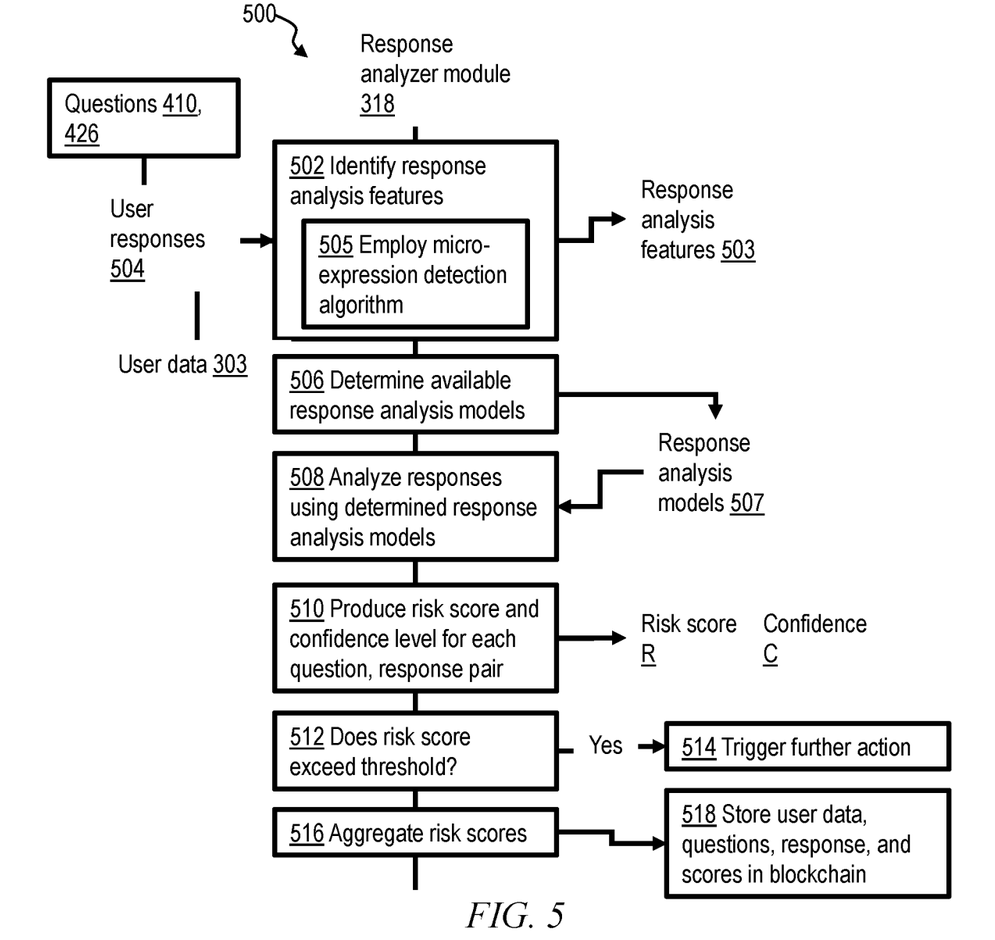
FIG. 5 depicts a flowchart of a method implemented by an exemplary response analyzer module of the system shown in FIG. 3.

FIG. 5 depicts the method 500 that is implemented by the response analyzer module 318. At 502, the response analyzer module 318 identifies response analysis features 503 in the first set of user data 303 and in user responses 504 that correspond to each of the questions 410, 426. The response analyzer module 318 analyzes the user responses corresponding to each presented questions on the user interface 504 to identify response analysis features to qualify either individual responses are accurate, unambiguous or require further verification. The various analysis factors 503 include: historic user responses for the same or similar question(s), user social media activities, user cognitive state, scope or purpose of questionnaire (e.g., screening for generic or specific blood donation, for organ donation, for stem cell donation, or for other medical tests), and other respondents of similar demography, medical history, or social profile. In one or more embodiments, at 505 the response analyzer module 318 employs a micro-expression detection algorithm, using non-invasive visual analytics, in order to learn the user affective, contextual and/or cognitive state (e.g., based on a real-time assessment such as confused, stressed) as it correlates to the user's cohort (e.g., education level, age, etc.) and to a given question (e.g., difficulty level, clarity of the question, etc.). The user affective, contextual and cognitive state is one of the response analysis features 503.

In one or more embodiments, at 506 the response analyzer module 318 compares a user's responses to responses from other users of a similar demographic, medical history, social profile, etc. in order to determine available response analysis models 507. In one or more implementations, the method of comparing a user's responses employs greedy or machine learning algorithms such as k-means algorithm, fuzzy clustering, and reinforcement learning. Given the teachings herein, the skilled artisan will be able to implement any of the examples of supervised, unsupervised or other machine learning algorithms as described. Also, when deploying one or more machine learning models, a computing device may be first tested in a controlled environment before being deployed in a public setting.

At 508, the response analyzer module 318 analyzes the responses using the determined response analysis models 507. As a result of the analysis, at 510 the response analyzer module 318 produces a risk score R for the <question, response> pair with a confidence level C, <question, response, R, C>. The risk scores R for the plurality of questions depend on the purpose of questionnaire, the cohort of the person being questioned, other static and dynamic user level and domain level features, etc. If at decision block 512 one of the computed risk scores R exceeds a threshold, then at 514 the response analyzer module 318 triggers further action (e.g., modify a question, generate a new question, add snippet information into the response-question pair for later examination). At 516 the response analyzer module 318 aggregates the risk scores R for all of the response-question pairs to obtain an aggregated score $R_a$ that measures the user's suitability for the sensitive service that is being screened. In one or more embodiments, the response analyzer module 318 adjusts the aggregated score based on results of physiologic tests (e.g., hemoglobin Hb, blood pressure, pulse test). At 518, the response analyzer module 318 stores the user data 303, the questions 410, 426, the responses 504, and the risk scores R in secured storage such as blockchain.

A non-exhaustive list of action examples include blood collection, lab testing prioritization, recommending specific lab tests, suggesting number of iterations for a particular test, recommending a specific machine to use, sending a notification to domain experts, etc. In one aspect, the action selector module 320 may use custom machine learning algorithms. Given an action space, and a state space (situation), a machine learning algorithm such as a neural network, can be used to estimate the confidence in the action(s) to be taken. The neural network model estimates parameters to choose a label (action). In one aspect, multiple labels (multi-class) can be estimated each with a confidence score. A set of actions having confidence score or scores above a threshold may be triggered to control content and/or a source of the content.

A neural network model which classifies or outputs actions to be performed is employed in one or more embodiments. A neural network model, for example, which is a fully connected network, may output or classify actions (e.g., provide confidence scores) given a vector of features as input representing the user questions, responses, user contextual stage, and service characteristics. In one aspect, the neural network, for example, is trained based on historical data comprising labeled training data which include input (user questions, responses, user contextual stage, and service characteristics) to output (actions) mappings. The neural network may be retrained periodically based on additional training data set.

Figure 6:
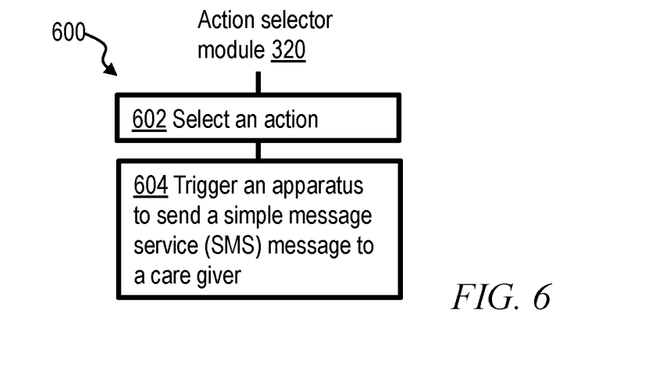
FIG. 6 depicts a flowchart of a method implemented by an exemplary action selector module of the system shown in FIG. 3.

For instance, FIG. 6 depicts an exemplary method 600 for selecting actions (e.g., blood test prioritization) in response to the analysis of the user responses, as implemented by the action selector module 320. At 602, the action selector module 320 (i.e., the neural network) selects an action. At 604, the action selector module 320 triggers an apparatus (e.g., a user device) to send a simple message service (SMS)

message to a care giver, i.e. a message instructing the care giver to perform the selected action (e.g., a sensitive service on the user).

The system 96 may help on-site/clinic decision makers (e.g., a nurse at a blood collection site), lab testers, etc. to prioritize tasks/operations, for example, by recommending what kind of further laboratory tests need to be done in response to the aggregated score and predicted testing of the blood and blood products. Example: A lifestyle category (LC) {<question, response, score>} pattern indicates that a user might be susceptible to a disqualifying condition. In the case of blood donation as a sensitive service, detecting the disqualifying condition through a questionnaire can reduce the significant cost to the blood banks associated with donations of unsuitable blood (wastage of blood kits, extensive testing processes, etc.).

In one or more embodiments, the system 96 provides secure document and data storage with access control to restrict access to generated questions, responses and user data. This can be implemented using blockchain. Furthermore, the system 96 supports multiple types of user interfaces, such as Web interfaces, mobile devices, portals, etc.

Given the discussion thus far, and with reference to the accompanying drawings, it will be appreciated that, in general terms, an exemplary method, according to an aspect of the invention, includes 301 receiving a first set of user data 303; 304 constructing a user profile 305 that incorporates the first set of user data in accordance with a sensitive service involving the user; 326 analyzing a situational context based on the first set of user data; 400 generating personalized questions responsive to the user profile and to the situational context, according to the sensitive service involving the user, and presenting the personalized questions to a user corresponding to the user data; 500 receiving and analyzing responses to the personalized questions from the user, including 505 detection of user micro-expressions related to at least some of the responses; 602 selecting, by a neural network, an action to be performed in response to analyzing the responses from the user, wherein the action is the sensitive service involving the user; and 604 triggering an apparatus to send a simple message service (SMS) message to a care giver, the message recommending performance of the sensitive service on the user. More generally, the system can recommend whether to perform a sensitive service in response to analyzing the responses from the user; triggering via an SMS is one non-limiting example. For example, a local computing device or a cloud server implementing a system according to one or more embodiments interfaces with a telecommunications network (e.g., via adaptor 20 discussed below) to cause the SMS message to be sent over the network to the care giver.

In one or more embodiments, the user data is received from a user information wallet 302.

In one or more embodiments, the first set of user data include one or more of social media activities 309, medical history 308, history of cognitive state 310, and history of question-response patterns 311.

In one or more embodiments, constructing the user profile includes characterizing the first set of user data into categories that comprise health category 312, lifestyle category 313, and domain category 314.

In one or more embodiments, characterizing the first set of user data includes determining occurrence of a user event in the first set of user data.

In one or more embodiments, the health category includes features extracted from at least one of user history, donor history, medical history, or medication history obtained from user computing devices.

In one or more embodiments, the domain category includes features extracted from at least one of a geographic positioning system, a weather station, a clock, a pressure sensor, and a news service.

In one or more embodiments, an apparatus triggers a simple message service (SMS) message to a care giver to perform a sensitive service on the user.

One or more embodiments of the invention, or elements thereof, can be implemented in the form of an apparatus including a memory and at least one processor that is coupled to the memory and operative to perform exemplary method steps, or in the form of a non-transitory computer readable storage medium embodying computer executable instructions which when executed by a computer cause the computer to perform exemplary method steps.

Figure 7:
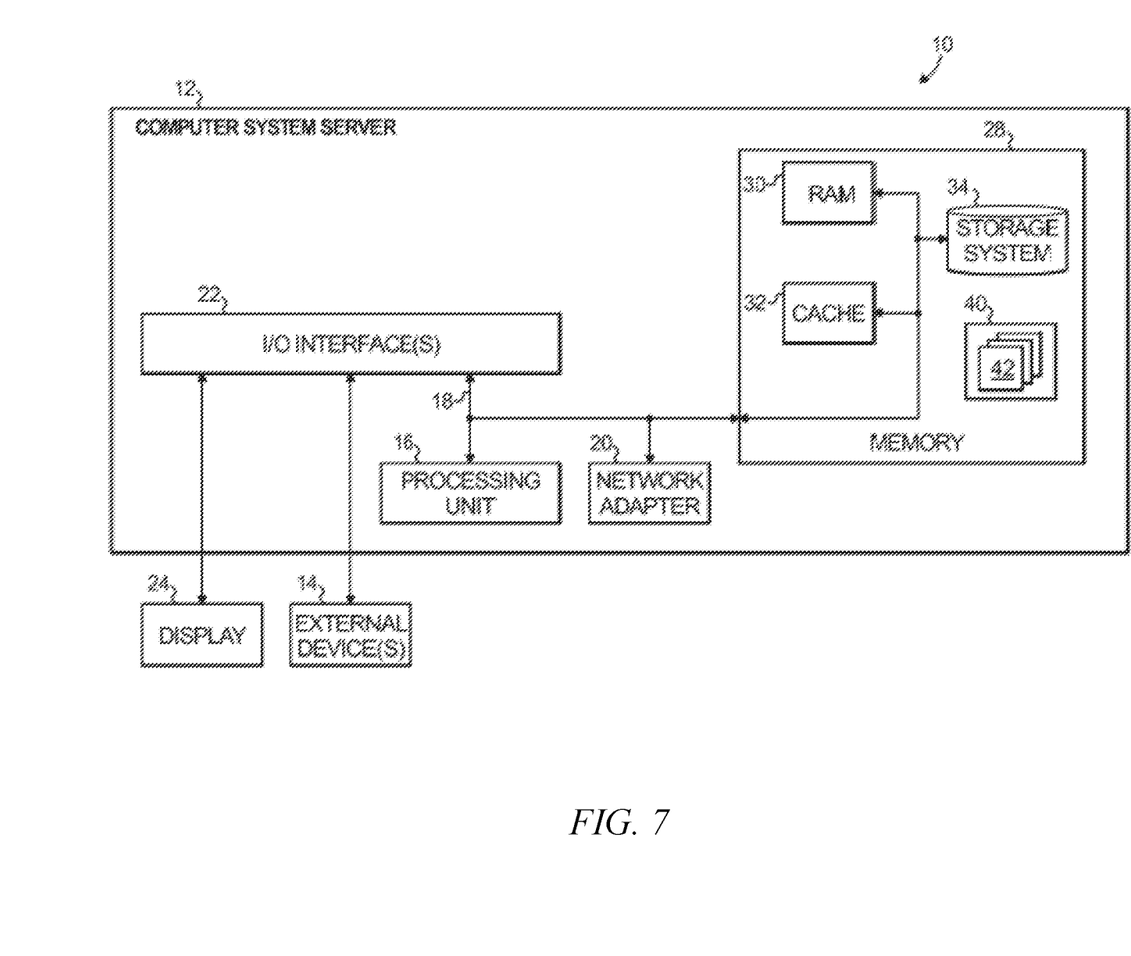
FIG. 7 depicts a computer system that may be useful in implementing one or more aspects and/or elements of the invention, also representative of a cloud computing node according to an embodiment of the present invention.

For example, in one or more embodiments, a processor 16 implements a user data gathering module 300 that receives the first set of user data 303 and constructs the user profile 305; a situational context analyzer module 324 that analyzes the situational context and updates the user profile; a personalized question generator module 316 that generates and presents the personalized questions; a question ranking module 317 that ranks features of the user profile in order to present the personalized questions in a ranked order; a response analyzer module 318 that assesses or analyzes user responses to the personalized questions, according to one or more machine learning models; and an action selector module 320, implemented in a neural network model, that recommends whether to perform a sensitive service in response to analyzing the responses from the user.

FIG. 7 depicts a computer system that may be useful in implementing one or more aspects and/or elements of the invention, also representative of a cloud computing node according to an embodiment of the present invention. Referring now to FIG. 7, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 7, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 7) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable cable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
receiving a first set of user data by a user data gathering module;
constructing, by the user data gathering module, a user profile that incorporates the first set of user data in accordance with a sensitive service involving the user;
analyzing, by a situational context analyzer module, a situational context based on the first set of user data;
passing the user profile from the user data gathering module to a personalized question generator module;
determining, by the personalized question generator module, a plurality of question generation models in response to an occurrence of a user event, constructing the user profile, analyzing the situational context and passing the user profile;
generating, by the personalized question generator module using the plurality of question generation models, personalized questions responsive to the occurrence of the user event, constructing the user profile, analyzing the situational context and passing the user profile, according to the sensitive service involving the user;
presenting the personalized questions to a user corresponding to the user data;
receiving video responses to the personalized questions from the user;
detecting, by non-invasive visual analytics, user facial micro-expressions related to at least some of the responses;
analyzing the responses from the user, including the user micro-expressions, according to one or more machine learning models selected from a list consisting of k-means algorithm, fuzzy clustering, and reinforcement learning;
assessing clarity of the personalized questions corresponding to the responses, based upon the analysis of the responses;
generating a second set of questions based on the responses to the personalized questions, on the micro-expressions, and on a user cohort analysis of the user;
elaborating at least one of the second set of questions, in response to the assessed clarity of one of the personalized questions, to explain the at least one of the second set of questions by providing at least one of textual, audio/video and graphical hints based on the user cohort analysis via the question presenter in at least one of the adaptive GUI and the interactive voice recognition interface;
receiving responses to the second set of personalized questions from the user;
training a neural network model on user questions and responses, user contextual stage, and service characteristics; and
selecting, by the neural network model, an action to be performed in response to analyzing the responses from the user, wherein the action is the sensitive service involving the user.

2. The method of claim 1 wherein the user data is received from a user information wallet.

3. The method of claim 1 wherein the first set of user data include social media activities, medical history, history of cognitive state, and history of question-response patterns.

4. The method of claim 1 wherein constructing the user profile further comprises characterizing the first set of user data into categories that comprise health category, lifestyle category, and domain category.

5. The method of claim 4 wherein characterizing the first set of user data includes determining occurrence of a user event in the first set of user data.

6. The method of claim 4 wherein the health category includes features extracted from at least one of user history, donor history, medical history, and medication history obtained from user computing devices.

7. The method of claim 4 wherein the domain category includes features extracted from a news service.

8. A non-transitory computer readable storage medium embodying computer executable instructions which when executed by a computer cause the computer to facilitate the method of:
receiving a first set of user data;
constructing a user profile that incorporates the first set of user data in accordance with a sensitive service involving the user;
analyzing a situational context based on the first set of user data;
determining a plurality of question generation models in response to an occurrence of a user event, constructing the user profile, and analyzing the situational context;
generating a first set of personalized questions using the plurality of question generation models, responsive to the occurrence of the user event, constructing the user profile and analyzing the situational context, according to the sensitive service involving the user;

presenting the first set of personalized questions to a user corresponding to the user data via a question presenter that displays the questions in at least one of an adaptive GUI and an interactive voice recognition interface;

receiving video responses to the personalized questions from the user;

detecting, by non-invasive visual analytics, user facial micro-expressions related to at least some of the responses;

analyzing the responses from the user, including the user micro-expressions, according to one or more machine learning models selected from a list consisting of k-means algorithm, fuzzy clustering, and reinforcement learning;

assessing clarity of the personalized questions corresponding to the responses, based upon the analysis of the responses;

generating a second set of questions based on the responses to the personalized questions, on the micro-expressions, and on a user cohort analysis of the user;

elaborating at least one of the second set of questions, in response to the assessed clarity of one of the personalized questions, to explain the at least one of the second set of questions by providing at least one of textual, audio/video and graphical hints based on the user cohort analysis via the question presenter in at least one of the adaptive GUI and the interactive voice recognition interface;

receiving responses to the second set of personalized questions from the user;

training a neural network model on user questions and responses, user contextual stage, and service characteristics;

selecting, by the neural network model, an action to perform in response to analyzing the responses from the user, wherein the action is a sensitive service to be performed on the user; and triggering the computer to send a simple messaging service (SMS) message that instructs a point of care service professional to perform the selected action.

9. The medium of claim 8, wherein the user data is received from a user information wallet.

10. The medium of claim 8, wherein the first set of user data include social media activities, medical history, history of cognitive state, and history of question-response patterns.

11. The medium of claim 8, wherein constructing the user profile further comprises characterizing the first set of user data into categories that comprise health category, lifestyle category, and domain category.

12. The medium of claim 11, wherein characterizing the first set of user data includes determining occurrence of a user event in the first set of user data.

13. The medium of claim 11, wherein the health category includes features extracted from at least one of user history, donor history, medical history, and medication history obtained from user computing devices.

14. The medium of claim 11 wherein the domain category includes features extracted from at least one of a geographic positioning system, a weather station, a clock, a pressure sensor, and a news service.

15. An apparatus comprising:
a memory embodying computer executable instructions; and
at least one processor, coupled to the memory, and operative, by executing the computer executable instructions, to facilitate a method of:
receiving a first set of user data;
constructing a user profile that incorporates the first set of user data in accordance with a sensitive service involving the user;
analyzing a situational context based on the first set of user data;
determining a plurality of question generation models in response to an occurrence of a user event, the construction of the user profile, and the analysis of the situational context;
generating personalized questions using the plurality of question generation models, responsive to the occurrence of the user event, the construction of the user profile and the analysis of the situational context, according to the sensitive service involving the user;
presenting the personalized questions to a user corresponding to the user data;
receiving video responses to the personalized questions from the user;
detecting, by non-invasive visual analytics, user facial micro-expressions related to at least some of the responses;
analyzing the responses from the user, including the user micro-expressions, according to one or more machine learning models selected from a list consisting of k-means algorithm, fuzzy clustering, and reinforcement learning;
assessing clarity of the personalized questions corresponding to the responses, based upon the analysis of the responses;
generating a second set of questions based on the responses to the personalized questions, on the micro-expressions, and on a user cohort analysis of the user;
elaborating at least one of the second set of questions, in response to the assessed clarity of one of the personalized questions, to explain the at least one of the second set of questions by providing at least one of textual, audio/video and graphical hints based on the user cohort analysis via the question presenter in at least one of the adaptive GUI and the interactive voice recognition interface; receiving responses to the second set of personalized questions from the user;
training a neural network model on user questions and responses, user contextual stage, and service characteristics;
selecting, by a neural network, an action to perform in response to analyzing the responses from the user and the micro-expressions, wherein the action is a sensitive service to be performed on the user; and
triggering the processor to instruct a point of care service professional to perform the sensitive service on the user.

16. The apparatus of claim 15 wherein the processor implements:
a user data gathering module that receives the first set of user data and constructs the user profile;
a situational context analyzer module that analyzes the situational context and updates the user profile;
a personalized question generator module that determines the question generation models, generates the personalized questions using the question generation models, and presents the personalized questions;
a question ranking module that ranks features of the user profile in order to present the personalized questions in a ranked order;

a response analyzer module that assesses user responses to the personalized questions; and an action selector module that recommends whether to perform a sensitive service in response to analyzing the responses from the user.

17. The apparatus of claim 15 wherein the apparatus triggers a simple message service (SMS) message to a point of care service professional to perform a sensitive service on the user.

18. The apparatus of claim 15 wherein the first set of user data include social media activities, medical history, history of cognitive state, and history of question-response patterns.

19. The apparatus of claim 15 wherein constructing the user profile further comprises characterizing the first set of user data into categories that comprise health category, lifestyle category, and domain category.

20. The apparatus of claim 19 wherein characterizing the first set of user data includes determining occurrence of a user event in the first set of user data.

21. The method of claim 1 further comprising assessing difficulty level of the personalized questions corresponding to the responses by detecting, by non-invasive visual analytics, user micro-expressions related to at least some of the responses.

* * * * *